(12) United States Patent
Glerum

(10) Patent No.: US 8,353,963 B2
(45) Date of Patent: Jan. 15, 2013

(54) EXPANDABLE SPACER AND METHOD FOR USE THEREOF

(75) Inventor: Chad Glerum, Pennsburg, PA (US)

(73) Assignee: Globus Medical, Audubon, PA (US)

( * ) Notice: Subject to any disclaimer, the term of this patent is extended or adjusted under 35 U.S.C. 154(b) by 288 days.

(21) Appl. No.: 12/615,806

(22) Filed: Jan. 12, 2010

(65) Prior Publication Data

US 2011/0172716 A1  Jul. 14, 2011

(51) Int. Cl.
*A61F 2/44* (2006.01)
(52) U.S. Cl. .................................... 623/17.16
(58) Field of Classification Search ............... 623/17.15, 623/17.16
See application file for complete search history.

(56) References Cited

U.S. PATENT DOCUMENTS

| | | | | |
|---|---|---|---|---|
| 4,863,476 | A * | 9/1989 | Shepperd | 623/17.15 |
| 6,723,126 | B1 * | 4/2004 | Berry | 623/17.11 |
| 2005/0113921 | A1 * | 5/2005 | An et al. | 623/17.11 |
| 2006/0149385 | A1 * | 7/2006 | McKay | 623/17.15 |
| 2006/0241621 | A1 * | 10/2006 | Moskowitz et al. | 606/72 |
| 2006/0241770 | A1 * | 10/2006 | Rhoda et al. | 623/17.15 |
| 2007/0255415 | A1 * | 11/2007 | Edie et al. | 623/17.16 |
| 2008/0147193 | A1 * | 6/2008 | Matthis et al. | 623/17.16 |
| 2009/0210061 | A1 * | 8/2009 | Sledge | 623/17.15 |
| 2010/0145456 | A1 * | 6/2010 | Simpson et al. | 623/17.16 |
| 2011/0160861 | A1 * | 6/2011 | Jimenez et al. | 623/17.16 |

* cited by examiner

*Primary Examiner* — Kevin T Truong
*Assistant Examiner* — David Bates

(57) ABSTRACT

An expandable implant is disclosed having an adjustable height for insertion between two adjacent bony structures or joint surfaces, for example between two adjacent spinal vertebrae. The implant includes at least one gear associated with at least one threaded shaft. Rotation of the gear engages the threaded shaft to expand the implant. The implant can be inserted in a collapsed configuration and expanded in situ. The invention also provides methods for using the implant to facilitate arthrodesis or fusion of adjacent joint surfaces or spinal vertebrae.

14 Claims, 6 Drawing Sheets

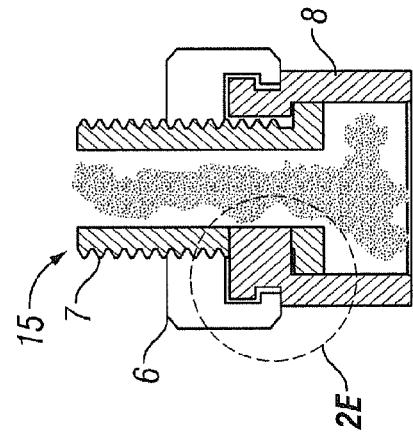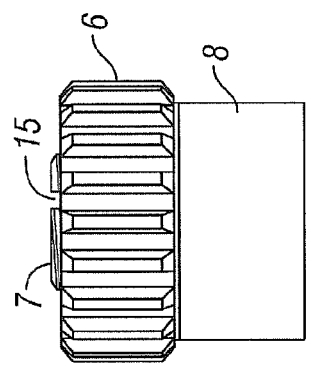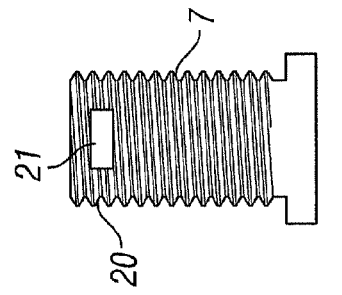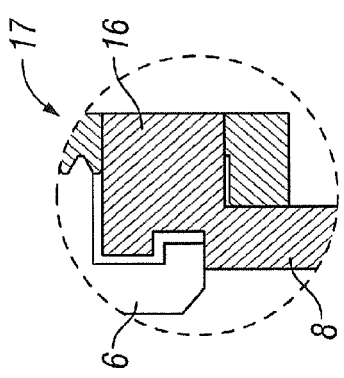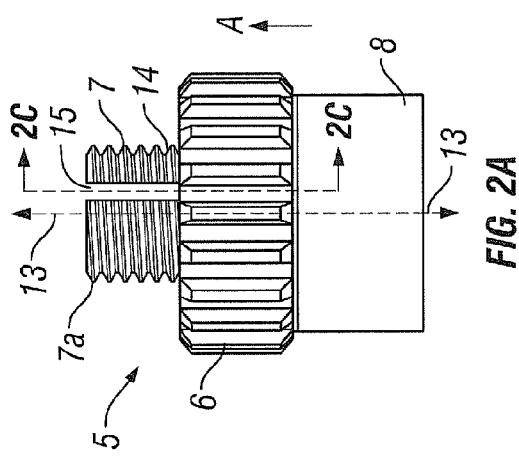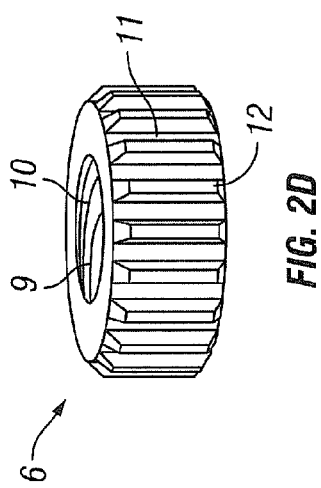

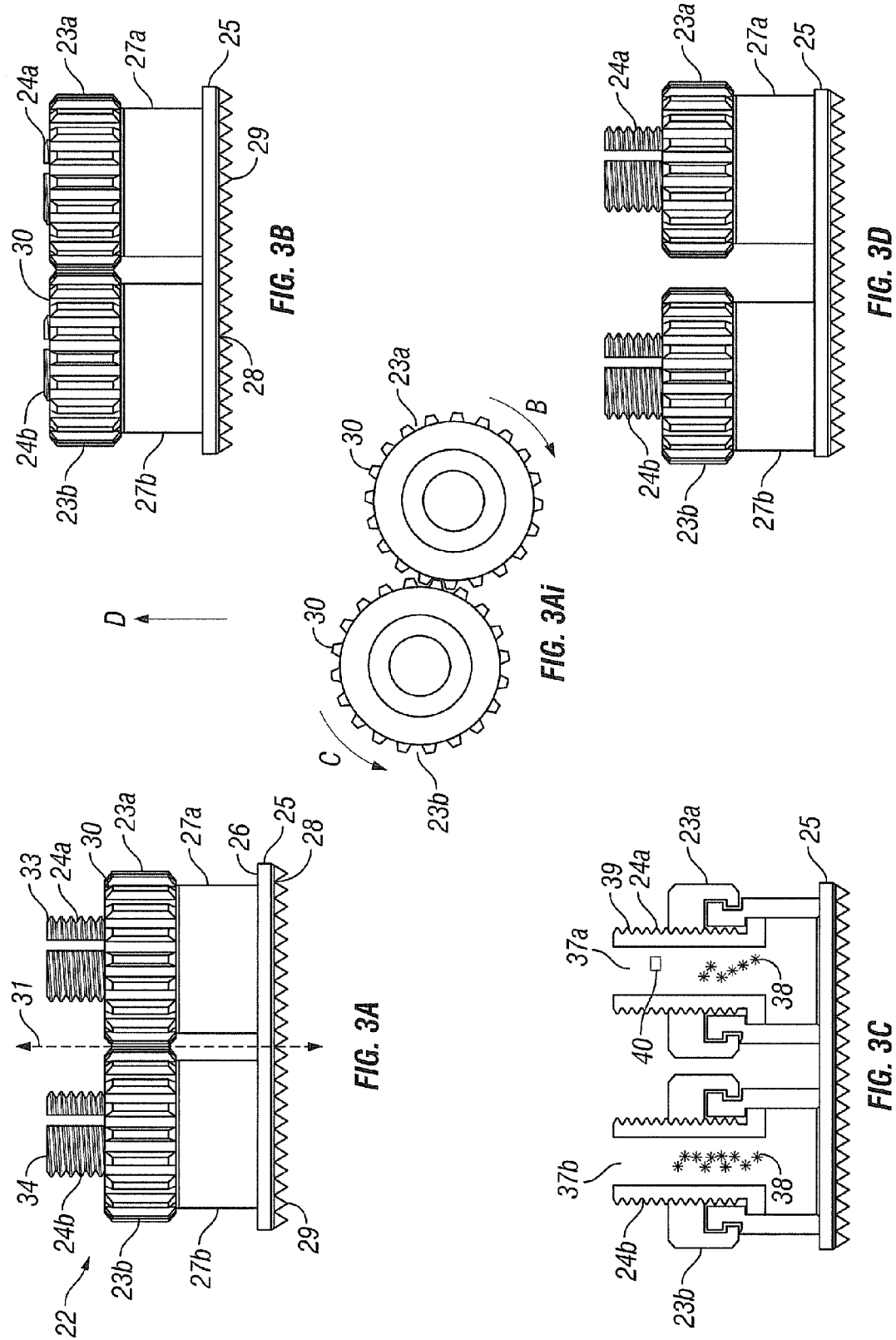

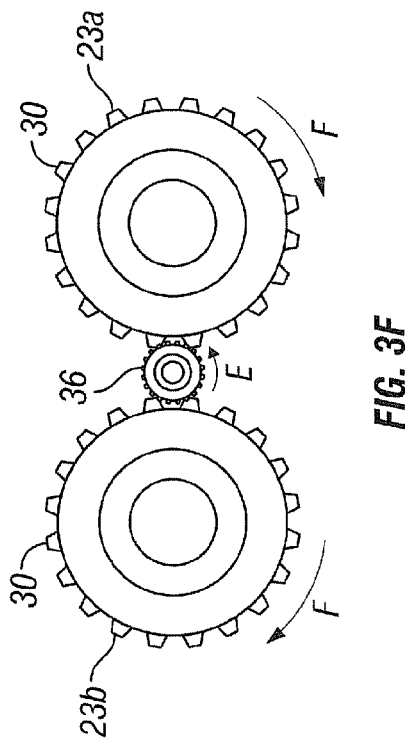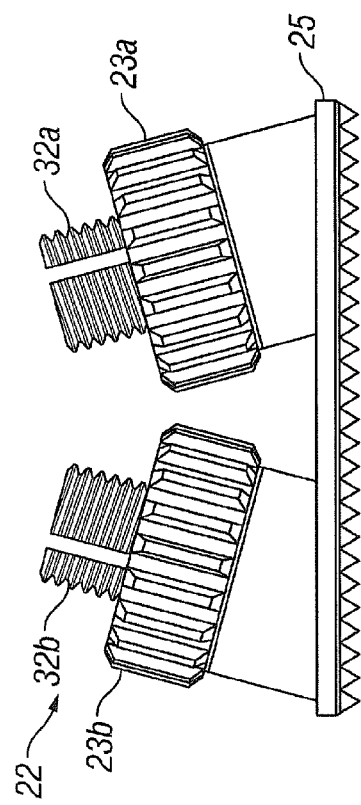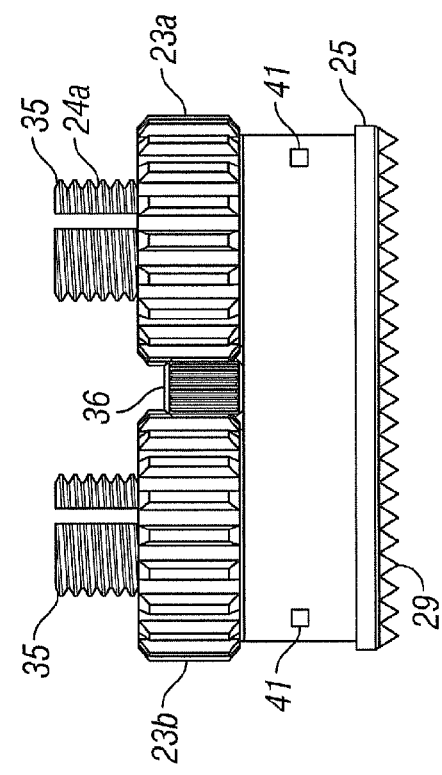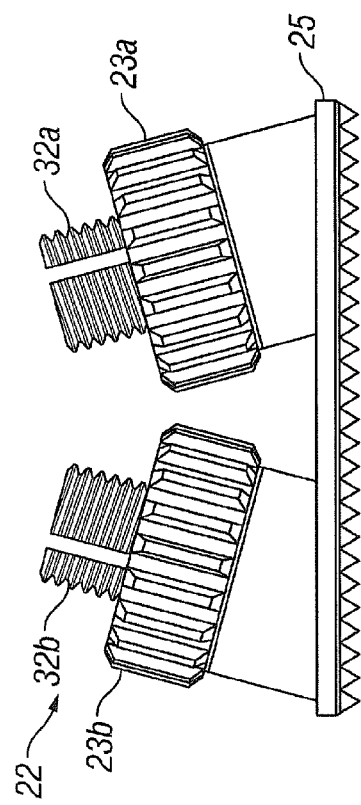

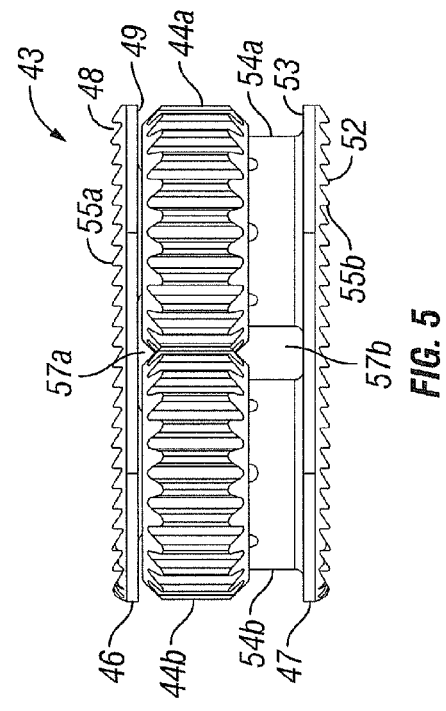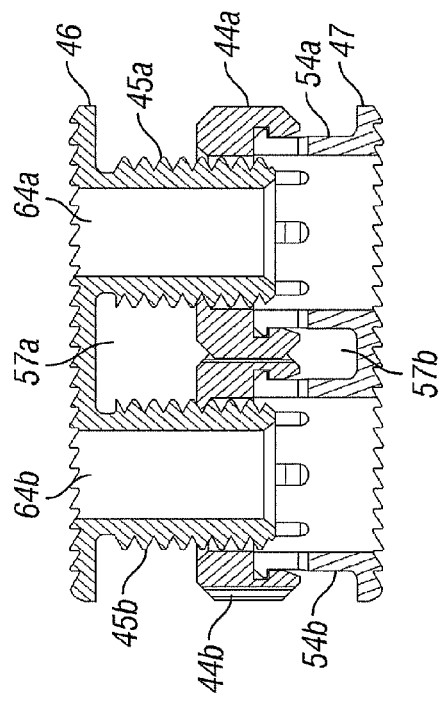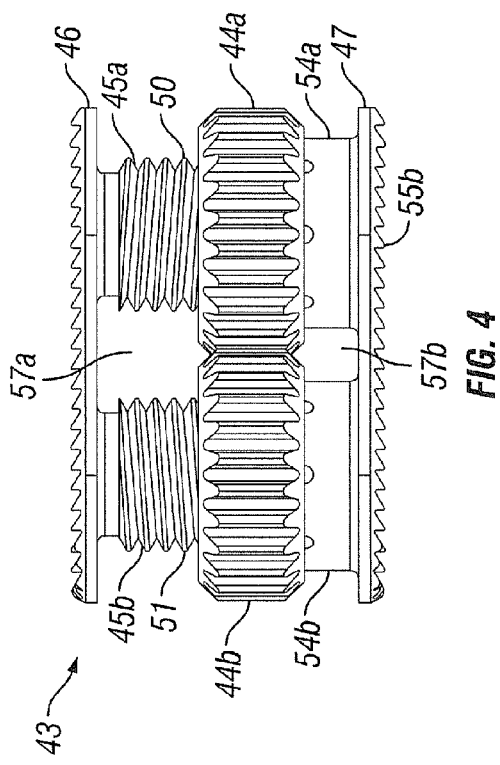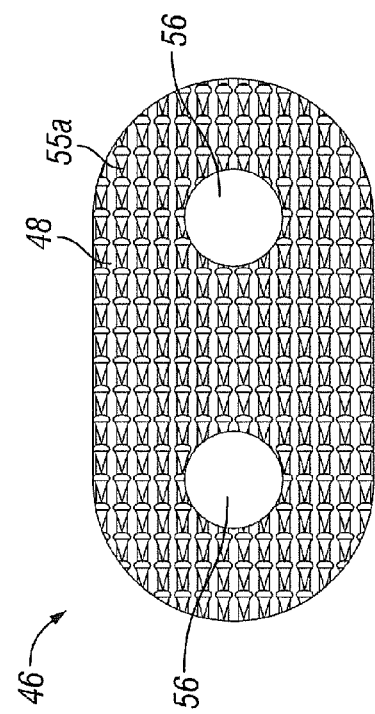

EXPANDABLE SPACER AND METHOD FOR USE THEREOF

FIELD OF THE INVENTION

The invention generally relates to spacers for use in orthopedic treatments, particularly to implants for insertion between two adjacent bony structures or two adjacent joint surfaces, and most particularly, to an expandable implant for insertion into the void remaining in the intervertebral space after removal of damaged disc material.

BACKGROUND

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, i.e. annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept/distribute external loads. The integrity of the composition and structure of the intervertebral disc is necessary to maintain normal functioning (of the intervertebral disc).

Many factors can adversely alter the composition and structure of the inteverterbral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves. Regardless of the cause, many of these disc pathologies become severe enough to require surgical intervention In most cases, this surgical intervention is a partial or complete removal of the damaged intervertebral disc material (discectomy). While the discectomy eliminates the problems associated with the damaged disc, it creates a void in the intervertebral space that, if left empty, can de-stabilize and possibly collapse the vertebrae, negatively affecting the whole vertebral column.

The stabilization of the spine has been a focus of medical research for over 100 years. Early efforts at stabilization included spinal fusion. Spinal fusion was first used to treat the symptoms of spinal tuberculosis (Pott's disease) including the collapse of vertebral bodies and abnormal curvature of the spine. In this technique, bone tissue was harvested from the patient and applied to the dorsal spine. See Ryerson, Dr. Edwin W., *The Journal of Bone and Joint Surgery*; s2-12:259-264, 1914; wherein treatment of patients using the bone-graft procedure developed by Dr. Fred Albee is discussed. The entire contents are incorporated herein by reference. Although this basic technique is still in use today, bone grafts alone are slow to fuse and may not be anatomically correct even if fusion is achieved. Furthermore, such bone grafts are often not strong enough to maintain long-term stability of the spine.

In order to facilitate solid fusion and further stabilize vertebrae, various implantable hardware systems have been devised. These systems are applied to the surface of the spine and can compress the bone graft area to accelerate fusion. For example, an instrument, such as a rod, is placed generally parallel to a patient's back and attached to selected vertebrae by screws, clips, hooks, and/or clamps. Although this type of system initially offers strength, the hardware can loosen over time decreasing this strength.

In addition to spinal stabilization hardware, an extensive variety of devices for placement within the intervertebral space has been developed. For example, Harms, et al. (U.S. Pat. No. 4,820,305) provides a prosthesis in the form of a hollow cylindrical jacket which acts as a "place holder" between vertebrae. Buettner-Janz, et al. (U.S. Pat. No. 4,759,766) provides an intervertebral disc endoprosthesis including two endplates with an intermediate spacing device. Other devices combine structural elements with bone graft material. For example, Bagby (U.S. Pat. No. 4,501,269) discloses an implantable basket. In order to insert the basket, a hole is bored transversely across a joint. The bone shavings are collected and placed in a basket that is slightly larger than the hole. The basket is then driven into the hole to spread the bones. The entire contents of the '305, '766, and '269 patents are incorporated herein by reference.

Brantigan (U.S. Pat. No. 5,192,327) provides an annular implant with rigid surfaces having spaces for packing of bone graft material. The rigid surfaces engage the adjacent vertebral bodies to resist displacement. The annular implant may be inserted singly or multiple implants can be inserted as a set. The implants of the set can have different thicknesses and are internally grooved to receive a connecting bar to bind the implants together. The entire contents of the Brantigan '327 patent are incorporated herein by reference.

Despite the enormous progress in spinal therapy, chronic back pain remains a perplexing problem and the number of patients with back problems continues to rise.

Thus, ongoing efforts are desired to improve treatments and curtail the problem.

SUMMARY OF THE INVENTION

An expandable implant having an adjustable height for insertion between two adjacent bony structures or two adjacent joint surfaces is disclosed. In one variation, the implant may include at least one gear, at least one threaded shaft, and a base or collar. The parts (gear, shaft, base) can be any size capable of functioning to expand the implant. Insertion of the implant facilitates arthrodesis or fusion of the bony structures or joints. Although intended to be useful with any adjacent bony structures or joint surfaces in which fusion is desired, the implant is particularly applicable to the spine, wherein it is inserted into the intervertebral space remaining after removal of damaged disc material.

In one embodiment, the implant includes a gear associated with a threaded shaft and a base. Rotation of the gear initiates rotation of the shaft to extend the shaft axially to the longitudinal axis of the implant. The shaft is extended to contact and engage one of the adjacent bony structures such that the bony structures are separated by the expanded implant. The threaded shaft has at least one side edge and a channel. The channel extends along the side edge parallel with the longitudinal axis of the shaft. The base is a housing for receiving the shaft and includes a projection, advantageously at a top end of the base, configured for engagement with the channel along the side edge of the shaft. The gear is coupled with the shaft and the base. Interior threading of the gear engages with the threading on the shaft. The engagement of the projection with the channel enables the rotation of the gear to extend the shaft, preventing rotation of the shaft in place.

In one embodiment, the implant includes a pair of actuation gears associated with at least two threaded shafts, and a base plate. Rotation of the gears initiates rotation of the threaded shafts to extend the shafts axially to the longitudinal axis of the implant. The base plate has an exterior surface and an interior surface. The interior surface of this plate includes a housing configured for receiving the at least two threaded shafts. As shown herein, a first threaded shaft and a second threaded shaft extend from the base plate in a substantially parallel configuration or in an angled configuration. The exterior surface of the base plate can additionally include a plurality of protrusions. The protrusions enhance engagement of the plate with the bony structures and may extend into the bone to stabilize and secure the implant in place.

Mechanical interaction of the pair of gears with the threaded shafts extends the shafts. The first gear of the pair is operably coupled with the first threaded shaft and the second gear of the pair is operably coupled to the second threaded shaft. Upon actuation, the first gear rotates in a first direction. This rotation of the first gear in the first direction initiates rotation of the second gear in a second direction opposite the first direction. This activation of the pair of gears rotates, and thus also, extends the shafts. The extended shafts contact and engage one of the adjacent bony structures such that the bony structures are separated by the expanded implant.

The threading and/or gears may be arranged in alternate ways. In the foregoing embodiment, the first and second threaded shafts exhibit opposite threading. For example, if the first threaded shaft has a right-handed thread, the second threaded shaft has a left-handed thread, or vice versa. If both shafts have the same type of threading, the gears can be uncoupled and another gear, or idler gear, placed between the two gears, enabling rotation of both gears in a same direction. Additional interposed gears may be employed to change a relative movement and/or direction between the driving gear and the driven gear.

In another embodiment, the shafts have the same or different direction of threading, but with differing thread pitch, enabling each shaft to rise at a different rate. Also, the pair of gears may be uncoupled such that the first threaded shaft and the second threaded shaft operate as single independent units. This arrangement enables each shaft to extend to a different height if needed, for example, to remove pressure from one area or to provide pressure to an injured area, or to adjust an angle of the two contacted bones.

In one embodiment, the implant includes a pair of actuation gears associated with at least two threaded shafts interposed between a top plate and a bottom plate. Rotation of the gears initiates rotation of the threaded shafts to extend the shafts axially to the longitudinal axis of the implant. The top plate includes an exterior surface and an interior surface. A first threaded shaft and a second threaded shaft extend from the interior surface in a substantially parallel configuration. As the top plate connects the two shafts, preventing rotation of the shafts, a channel in a side of a shaft, and a cooperating projection from the base, are not needed to prevent a rotation of a shaft.

Further, as the shafts are connected, the first and second threaded shafts exhibit opposite threading. For example, if the first threaded shaft has a right-handed thread, the second threaded shaft has a left-handed thread, and vice versa. Or if both shafts have the same type of threading, the gears can be uncoupled and another gear placed therebetween, to establish a common direction of rotation.

The bottom plate also has an exterior surface and an interior surface. The interior surface of this bottom plates includes a housing configured for receiving the first and second threaded shafts. One or both of the exterior surfaces of the top and bottom plate can additionally include a plurality of protrusions. The protrusions enhance engagement of the plates with the bony structures and may extend into the bone to stabilize and secure the implant in place.

Mechanical interaction of the pair of gears with the threaded shafts extends the top plate. The first gear of the pair is operably coupled with the first threaded shaft and the second gear of the pair is operably coupled to the second threaded shaft. Upon actuation, the first gear rotates in a first direction. This rotation of the first gear in the first direction initiates rotation of the second gear in a second direction opposite the first direction. This activation of the pair of gears rotates the shafts to extend the top plate. The extended top plate contacts and engages one of the adjacent bony structures such that the bony structures are separated by the expanded implant.

In any embodiment, the gears can be rotated by manually engaging the exterior teeth or surface of a gear using fingers or a tool, or the rotation can be robotically assisted.

A motor, powered by electricity, hydraulic pressure including for example air or water, or other form of propulsion may be used to drive one or more gears to extend a shaft. The motor may be remotely controlled, in a manner known in the relevant art. A power source may be implanted within the patient to power the motor.

Any of the described implants can be used to achieve distraction (of the bony surfaces) without the necessity of a distraction tool. A distraction tool applies force to displace the bony surfaces. Conventional implants often require a distraction device, for example as disclosed by Ray (U.S. Pat. No. 6,599,292 B1, the entire contents of which are incorporated herein by reference), for insertion and positioning within the disc space. Furthermore, conventional implants, which are capable of applying enough force to accomplish adequate distraction of vertebral bodies, can be too large to be inserted via minimally-invasive incisions. Moreover, the use of each additional tool imposes further risk to the patient. The invention advantageously reduces the number of tools needed to safely accomplish the objectives of distraction and or support.

When in the collapsed configuration, the implant of the invention can be gently inserted through a small incision using any appropriate minimally-invasive procedure. The implant is then expanded in situ, wherein the expansion itself distracts the vertebrae without undesirable distraction force imposed elsewhere in the body, including for example an expansion of the incision. Reduction of the force applied, and area of applied force, when inserting the implant of the invention renders the procedure safer and less painful for the patient during recovery, with a shorter required recovery period.

In the embodiments including plates, the top plate, bottom plate, or both plates can additionally include at least one opening or aperture through which therapeutic material may be inserted into an area between the interior surface of the top plate and the interior surface of the bottom plate, for example within the shafts, or alternatively through other means of confinement of the material, for example netting or other containment surfaces. The hollow spaces may pass into the threaded shafts, wherein the shafts provide a receptacle for the inserted material. The material can include any of the following: osteogenic material, such as bone graft material, growth factors, differentiation factors, healing agents, analgesics, or antimicrobial agents.

Upon installation, the openings or apertures through the plates allow for bone growth into the interior spaces such that any new bone growth present therein can contact and fuse therethrough with the existing bone to further stabilize the implant and/or the bony structures.

Furthermore, in addition to access through a top or bottom plate, any of the threaded shafts can have a hollow interior space accessible through an opening near a shaft end, accessible when the device of the invention has been installed. In this manner, additional material may be inserted after a shaft has been expanded, where the interior volume of the shaft has been increased. In this manner, the material may extend from a surface of a first bone to a surface of a second bone, promoting, for example, contiguous bone growth.

The invention includes methods for using the described implants to facilitate arthrodesis or fusion of adjacent bony surfaces or joint surfaces, including, but not limited to spinal vertebrae. Although this method is advantageously used with vertebrae, it is contemplated for use with any adjacent bones and/or bony structures. The steps include accessing the two adjacent bony surfaces to be fused in the patient's body, providing the implant in the collapsed configuration, preparing the space between the bony surfaces for insertion of the implant, inserting the implant, actuating the gear or gears, extending the shafts and or any associated plates to the expanded configuration to engage one or more of the adjacent bony surfaces, and then closing the surgical site in an accepted manner.

In addition to the aforementioned projections, devices of the invention may be further secured against displacement, for example, by inserting fasteners through a portion of the device, into surrounding tissue. For example, an aperture may be provided in a top or bottom plate, and a bone screw may be inserted therethrough in a manner known in the art to secure the device to the associated bone. Adhesive or other methods known to one skilled in the art may also be used for this purpose.

Further, an undesired rotation of a gear, or movement of a shaft, may be prevented by applying an adhesive between a gear and the body, a shaft and the body, or a gear and a shaft, for example. In order to enable a future adjustment of the device, removable adhesive is advantageous. Alternatively a set screw or through screw may be provided to secure any moving part of the device, to prevent movement of same once an advantageous position has been established.

Devices in accordance with the invention are useful for spacing and distraction in many different orthopedic treatments.

Devices of the invention thus provide: an expandable implant having an adjustable height; an expandable implant having a first, collapsed height prior to expansion and a second, expanded height after expansion; an implant that can be inserted via a minimally-invasive surgical procedure and expanded in situ; an implant that can be inserted via a minimally-invasive surgical procedure and expanded in situ to restore the height of an intervertebral disc space; an implant that can achieve distraction without the necessity of a distraction tool; an expandable implant which can be adjusted intraoperatively, for example, the implant can be collapsed, expanded, and re-fitted if a previous attempt to fit it is unsatisfactory or a condition has changed; an expandable implant for insertion between two adjacent bony structures; an expandable implant for insertion between two adjacent joint surfaces; an expandable implant for insertion between two adjacent spinal vertebrae; an expandable implant for facilitation of arthrodesis or fusion of two adjacent bony structures; an expandable implant for facilitation of arthrodesis or fusion of two adjacent joint surfaces; an expandable implant for facilitation of arthrodesis or fusion of two adjacent spinal vertebrae; an expandable implant for restoring the height and shape of an intervertebral disc space after removal of damaged disc material; and/or an expandable implant for treatment of degenerative disc disease (DDD).

The implant advantageously supplements and/or replaces disc material such that degenerated discs can be removed from the patient without destroying the structure/function of the spinal motion segment.

Other aspects of the invention include providing: an in vivo receptacle for material; an in vivo receptacle for osteogenic material; an implant containing bone graft material; an implant containing bone graft material and an effective amount of a growth factor or differentiation factor; an expandable implant that expands via interaction of an associated threaded gear(s) with a threaded shaft; an expandable implant having a gear associated with a threaded shaft and a base; an expandable implant having a pair of actuation gears associated with at least two threaded shafts, and a base plate; an expandable implant having a pair of coupled actuation gears with at least two associated threaded shafts interposed between a top plate and a bottom plate; an expandable implant having a pair of uncoupled gears; an expandable implant having a pair of mated gears; an expandable implant which is mechanically activated via right-handed left-handed threading; an implant having at least two threaded shafts with the same type of threading; an implant having at least two threaded shafts with the same type of threading, but with different pitches of the threading; an expandable implant including at least two threaded shafts having the same type threading and idler gear separating a driver gear and a driven gear; an implant that is capable of achieving distraction of bony structures without the necessity of a distraction tool; an implant that is capable of achieving distraction of joint surfaces without the necessity of a distraction tool; an implant that is capable of achieving distraction of spinal vertebrae without the necessity of a distraction tool.

Further aspects of the invention provide: a method for facilitating fusion of two adjacent bony structures in a patient; a method for facilitating fusion of two adjacent joint surfaces in a patient; a method for facilitating fusion of two adjacent spinal vertebrae in a patient; a method for restoring the height and shape of an intervertebral disc space after removal of damaged disc material; a method for treating degenerative disc disease (DDD) by using the described implants to replace degenerated discs and thus, restore structure and function to the spinal motion segment; a method for distracting bony structures; a method for distracting joint surfaces; and/or a method for distracting vertebral bodies; a method for distracting vertebral endplates.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings, when considered in conjunction with the subsequent detailed description. The embodiments illustrated in the drawings are intended only to exemplify the invention and should not be construed as limiting the invention to the illustrated embodiments, in which:

FIG. 2A is a front plan view of one embodiment of the implant in an expanded configuration;

FIG. 2B is a front plan view of the implant shown in FIG. 2A in the collapsed configuration;

FIG. 2C is a front cross-sectional view of the implant shown in FIG. 2A;

FIG. 2D is a cross-sectional view of the gear shown in FIG. 2A;

FIG. 2E is an enlarged cross-sectional view of the engagement of the channel and the projection of the implant shown in FIG. 2A;

FIG. 2F is a front view of the threaded shaft of the implant shown in FIG. 2A;

FIG. 3A is a front plan view of another embodiment of the implant in an expanded configuration;

FIG. 3Ai is top view of the gears of the implant shown in FIG. 3A;

FIG. 3B is a front plan view of the implant shown in FIG. 3A in the collapsed configuration;

FIG. 3C is a front cross-sectional view of the implant shown in FIG. 3A;

FIG. 3D is a front plan view of the implant shown in FIG. 3A with uncoupled gears in an expanded configuration;

FIG. 3E is a front plan view of an embodiment of the implant with idler gears in the expanded configuration;

FIG. 3F is a top view of the idler gears of the implant shown in FIG. 3E;

FIG. 3G is a front plan view of the base plate of the implant shown in FIG. 3A having an attached wedge tool;

FIG. 3H is a front plan view of an embodiment of the implant in the expanded configuration having shafts in an angled configuration;

FIG. 4 is a front plan view of another embodiment of the implant in an expanded configuration;

FIG. 5 is a front plan view of the implant shown in FIG. 4 in the collapsed configuration;

FIG. 6 is a top plan view of the top plate of the implant shown in FIG. 4;

FIG. 7 is a front cross-sectional view of the implant shown in FIG. 4;

DETAILED DESCRIPTION

Figure 1:
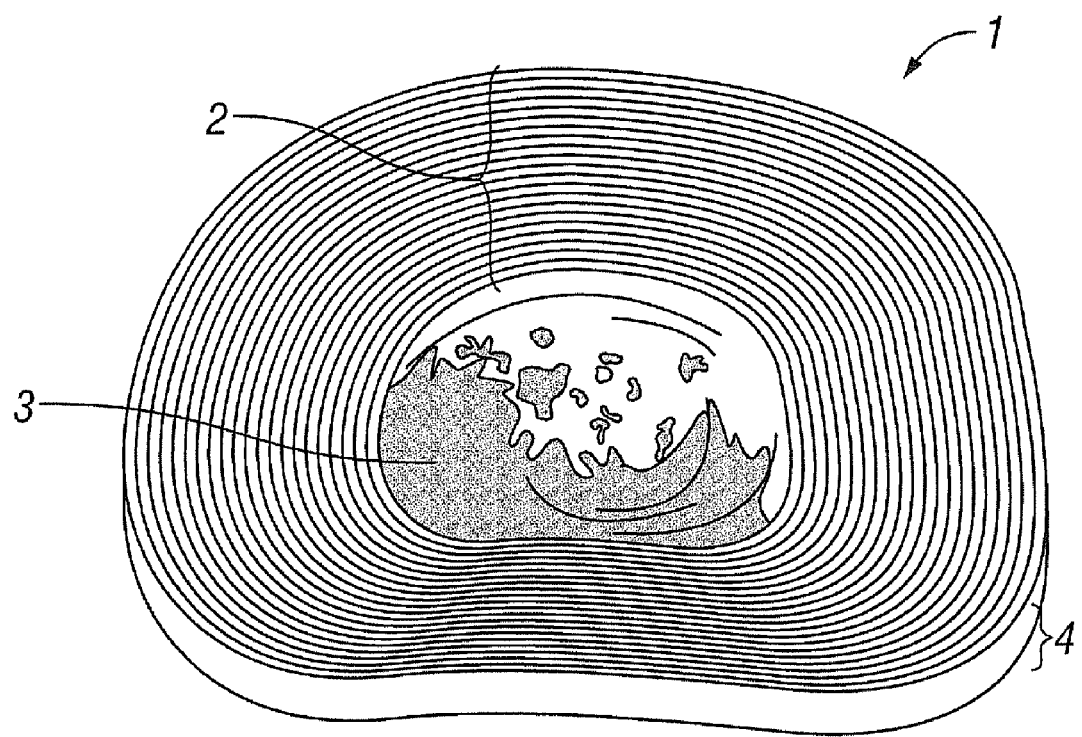
FIG. 1 is a perspective view of a healthy intervertebral disc.

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described implants, methods, and any further application of the principles of the invention as described herein, are contemplated as would normally occur to one skilled in the art to which the invention relates. The implants described herein are not limited to the specific embodiments.

In general, the invention provides an expandable implant having an adjustable height. The implant is inserted between two adjacent bony surfaces to facilitate fusion of the bony surfaces. Although intended to be useful with any adjacent bony surface in which fusion is desired, the implant is advantageously applied to insertion between two adjacent vertebral bodies in any section of the spine, including the cervical, thoracic, lumbar, and sacral vertebral sections. Any number or type of implant can be used in a patient, for example, insertion of an implant having two threaded shafts between lumbar vertebrae and insertion of an implant having one threaded shaft between two cervical vertebrae. The use of multiple implants is particularly advantageous for patients whose back pain is not limited to a localized area or patients whose localized damage has progressed to other areas of the spine.

Any one or all of the members of the implants can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

The implant can be manufactured using any method for making objects out of these materials. Particularly applicable are methods for molding plastics, for example injection molding or blow molding. Blow molding is particularly useful for manufacture of hollow parts such as the threaded shafts. Also applicable are methods for cutting metal and/or for making metal parts, for example, shearing, laser cutting apparatus, and waterjets. The implant can be manufactured as a whole or fabricated from individual parts. The parts may be snapped or welded together in a number of different ways. A gear can be coupled with a shaft and then mounted to a base. A gear can be mounted to a base and the shaft inserted therein.

After assembly, the implants can be sterilized and packaged. Sterilization can be accomplished by autoclave, ultraviolet lamp, bleach solutions, alcohol solutions, and/or combinations thereof. The implants can be packaged individually or in groups using any material suitable for packaging medical items.

The implant and methods for its insertion can be used in a treatment protocol for any condition in a patient involving diseased or damaged bony structures. The patient can be a human being. Additionally, it is contemplated that the implant may be useful in veterinary science for any animal having adjacent bony structures to be fused. The implant can collapse, for example, to approximately one half of its expanded size. When in this collapsed configuration, the implant can be inserted into a space through a small incision and narrow pathways using appropriate minimally-invasive techniques, positioned across the space, and expanded to the desired height. The incision may be short, for example about one inch in length, smaller than the implant in an expanded configuration. If the desired position and/or expansion are not achieved, the implant can be collapsed, repositioned, and expanded in situ.

Although the implant is exemplified herein for use in the spine, the implant is contemplated for fusion of any bony structures. Whilst the implants are described herein using several embodiments, the implants are not limited to these embodiments. An element of one embodiment may be used in another embodiment or an embodiment may not include all described elements.

Referring now to the figures, a healthy intervertebral disc 1 is illustrated in FIG. 1. The intervertebral disc 1 includes a gel-like center, the nucleus pulposus 3, surrounded by a fibrous ring, the annulus fibrosis 2. The relationship between the structure and function of the nucleus pulposus 3 and the annulus fibrosis 2 is essential to maintain health of the intervertebral disc 1. A healthy nucleus pulposus 3 exhibits hygroscopic properties. For example, as the disc 1 absorbs water, the intra-nuclear pressure increases, swelling the nucleus pulposus 3 expanding the height 4 of the disc, and in turn, tensioning the fibers of the annulus fibrosis 2. Many factors can adversely alter the structure and function of the intervertebral disc, such as normal physiological aging, mechanical injury/trauma, and/or disease. Since the disc is avascular any damage is, more often than not, irreversible. Damaged discs are either partially or fully removed, leaving space between the adjacent vertebrae.

The expandable implant of the invention is suitable for insertion into the intervertebral space to restore the height and shape of the space. The implant has a first, collapsed height and a second, expanded height.

In the embodiment illustrated in FIGS. 2A-2F, the implant 5 includes a gear 6 operably coupled with a threaded shaft 7 and a base 8. Base 8 is housing for receiving threaded shaft 7. The first, collapsed configuration of implant 5 is shown in FIG. 2B and the second, expanded configuration in FIG. 2A. The expandable configuration is adjustable and can be set in any position along the length of the partially or fully extended threaded shaft 7. The interior surface 9 of gear 6 has threads 10 and the exterior surface 11 has teeth 12 (FIG. 2D). The rotation of gear 6 can be initiated manually, or by engaging teeth 12 with a tool. Alternatively, rotation may be initiated with robotic assistance. The rotation of gear 6 initiates rotation of shaft 7, the rotation extending the shaft 7 in a direction axial (indicated by arrow A in FIG. 2A) to the longitudinal axis 13 of the implant 5. The threading 10 of gear 6 engages with the threading 7a of shaft 7 to produce axial movement of shaft 7. Shaft 7 can be extended until it separates the adjacent bony surfaces by contacting and engaging one or more of the adjacent bony surfaces. Threaded shaft 7 has at least one side edge 14 and a channel 15. Channel 15 extends along side edge 14 parallel to longitudinal axis 13 forming an indented groove. The base 8 includes a projection 16 near a top end 17 (FIG. 2E). Projection 16 engages with channel 15 to prevent threaded shaft 7 from rotating in place. The projection 16 engages along the length of channel 15 until the desired extension is reached.

A stop may be provided to prevent overextension, for example the channel may stop (not shown) along side edge 14, or threads may discontinue along shaft 7. The engagement of channel 15 and projection 16 is illustrated in FIG. 2E. Threaded shaft 7 can be hollow forming a space which can function as a receptacle 18 for inserted material 19 (FIG. 2C).

The hollow interior 18 is accessible through a hole or aperture 21 at a top end 20 of shaft 7 (FIG. 2F). The inserted material 19 can include osteogenic material, bone graft material, growth factors, differentiation factors, hormones, cytokines, and combinations thereof.

After installation of the implant 5, inserted material 19 can maintain contact with the bone through aperture 21. This contact facilitates fusion of the bony surfaces. Although the implant 5 does not require any supplemental fixation, further fixation of the implant in the body can be accomplished with the installation of devices such as rods, screws, and plates.

In the embodiment illustrated in FIGS. 3A-3H, the implant 22 includes a pair of actuation gears (23a and 23b) operably coupled with at least two threaded shafts (24a and 24b) and a base or bottom plate 25. Although this embodiment is exemplified by two threaded shafts, three or more shafts may be used. Although, in FIG. 3A the threaded shafts 24a and 24b are shown as extending from the base plate 25 in a substantially parallel configuration an angled extension of the threaded shafts is also contemplated. In an embodiment of the implant 22i, the threaded shafts 32a and 32b are shown in FIG. 3H in an angled configuration.

The first, collapsed configuration of implant 22 is shown in FIG. 3B and the second, expanded configuration in FIG. 3A. The expandable configuration is adjustable and can be set in any position along the length of the partially or fully extended threaded shafts 24a and 24b. The base plate 25 has an exterior surface and an interior surface. The interior surface 26 of the base plate 25 includes a housing (27a and 27b) configured for receiving the at least two threaded shafts (24a and 24b).

As shown in FIG. 3C, gears 23a, 23b are retained in rotatable connection to bottom plate 25 by an interlocking projection 25A in bottom plate 25, and groove 23D in gear 23a, although a groove may be provided in bottom plate 25 and a corresponding projection in gear 23b. Alternative means of rotatably retaining gear 23a, 23b upon bottom plate 25 may be provided, as would be understood to one skilled in the art.

The exterior surface 28 of the base plate 25 can include a plurality of protrusions 29. The protrusions 29 enhance engagement of the base plate 25 with the bony surface and can extend into the bone to stabilize and secure the implant in place. This stabilization may reduce the chances for dislodgement over the life of the implant.

A wedge 42 can be attached to or incorporated within base plate 25 (FIG. 3G). Wedge 42 enables an angular displacement of base plate 25, to preserve or establish a correct angular displacement of bones between which device 22 is implanted.

Gear 23a is operably coupled with threaded shaft 24a and base plate 25. Gear 23b is operably coupled with threaded shaft 24b and base plate 25. The rotation of gear 23a can be initiated manually, or by engaging teeth 30 with a tool. Alternatively, rotation may be initiated with robotic assistance. Gear 23a rotates in a first direction indicated by Arrow B. This rotation in a first direction initiates rotation of gear 23b in a second direction indicated by Arrow C. This second direction is opposite that of the first direction. For example, if gear 23a is rotating in a clockwise direction, gear 23b rotates in a counterclockwise direction (FIG. 3Ai). The rotation of gears 23a and 23b initiates rotation of threaded shafts 24a and 24b, the rotation extending the shafts 24a and 24b in a direction axial (indicated by arrow D) to the longitudinal axis 31 of the implant 22. The shafts 24a and 24b can be extended until they separate the adjacent bony surfaces by contacting and engaging one of the adjacent bony surfaces.

The threading and gears of implant 22 can be arranged in various ways to provide a wide range of treatment options.

The threading of each shaft may be of the same or different pitches. The shafts can exhibit the same or opposite threading. For example, in the implant 22 shown in FIG. 3A, the threaded shafts 24a and 24b exhibit opposite threading, i.e. shaft 24a has a left-handed thread 33 and shaft 24b has a right-handed thread 34. If the shafts have equivalent threading 35, gears 23a and 23b can be uncoupled and a third gear 36 placed there between (FIGS. 3E and 3F). Gear 36 rotates in an opposite direction (indicated by Arrow E) from the direction (indicated by Arrows F) of gears 23a and 23b (FIG. 3F).

Alternatively, the gears 23a and 23b can be uncoupled, and threaded shafts 24a and 24b can operate independently of each other. An embodiment of the implant 22ii has uncoupled gears 23a and 23b (FIG. 3D). This arrangement enables each shaft to extend to a different height, if necessary, for example, to remove pressure from one area or to provide pressure to an injured area such a bone fracture.

Either or both threaded shafts 24a and 24b can be hollow forming spaces which can function as receptacles 37a and 37b for inserted material 38. For example, as shown in FIG. 3C, the hollow interior 37a of shaft 24a is accessible through a hole or aperture 40 at a top end 39. The inserted material 38 can include osteogenic material, bone graft material, growth factors, differentiation factors, hormones, cytokines, and combinations thereof. After installation of the implant 22, inserted material 38 can maintain contact with the bone through aperture 40. This contact facilitates fusion of the bony surfaces. Although the implant 22 does not require any supplemental fixation, further fixation of the implant in the body can be accomplished with the installation of devices such as rods, screws, and plates. Openings 41 for installation of such devices are shown in FIG. 3E.

In the embodiment illustrated in FIGS. 4-9, the implant 43 includes a pair of actuation gears (44a and 44b) associated with at least two threaded shafts (45a and 45b) interposed between a top plate 46 and a bottom plate 47. Although this embodiment is exemplified by two threaded shafts, three or more shafts may be used. The first collapsed configuration of implant 43 is shown in FIG. 5 and the second, expanded configuration in FIG. 4. A cross-sectional view of the implant of FIG. 4 is shown in FIG. 7 in an expanded configuration.

The top plate 46 has an exterior surface 48 and an interior surface 49, the interior surface 49 including at least a first threaded shaft 45a and a second threaded shaft 45b extending from or connected thereto. The first threaded shaft 45a and the second threaded shaft 45b are substantially parallel. The first 45a and second 45b threaded shafts exhibit opposite threading, 50 and 51. For example, if the first threaded shaft 45a has a left-handed thread 50, the second threaded shaft 45b has a right-handed thread 51 and vice versa.

The bottom plate 47 also has an exterior surface 52 and an interior surface 53, the interior surface 53 including a first housing 54a configured for receiving the first threaded shaft 45a and a second housing 54b configured for receiving the second threaded shaft 45b.

Mechanical interaction of the pair of gears 44a and 44b with the threaded shafts 45a and 45b extends the top plate 46. The first gear 44a of the pair is operably coupled with the first threaded shaft 45a and the second gear 44b of the pair is operably coupled to the second threaded shaft 45b. Upon actuation, the first gear 44a rotates in a first direction. This rotation of the first gear 44a in the first direction initiates rotation of the second gear 44b in a second direction opposite the first direction (FIG. 3Ai). This activation of the pair of gears 44a and 44b rotates the shafts 45a and 45b to extend the top plate 46. The extended top plate 46 contacts and engages one of the adjacent bony surfaces such that the bony structures are separated by the expanded implant.

Shaft 45a is displaced by being urged by moving threads associated with gear 44a, wherein a thread face of gear 44a pushes against a thread face of shaft 45a. As shaft 45a may only move in a longitudinal direction, the rotational movement of gear 44a is translated to cause a corresponding longitudinal movement of shaft 45a.

On one or both of the exterior surfaces of the top and bottom plates 48 and 52 can include a plurality of protrusions 55a and 55b, respectively. The protrusions enhance engagement of the plates with the bony structures and contact and/or may additionally extend into the bone to stabilize and secure the implant in place. This mechanism limits the possibility for dislodgement or loosening of the implant over time such that the patient is provided with a long-lasting device requiring limited adjustments and/or replacement.

Referring now to FIG. 6, in an embodiment of the implant, the top plate 46, bottom plate 47, or both plates can additionally include at least one opening or aperture 56 through which material may be inserted into a first hollow space 57a or second hollow space 57b between the interior surface of the top plate 49 and the interior surface of the bottom plate 53. The size of the first hollow space 57a increases as the top plate 46 is expanded (illustrated in FIG. 4 and FIG. 7). Furthermore, either or both threaded shafts 45a and 45b can be hollow forming spaces which can function as receptacles 64a and 64b for inserted material (FIG. 7).

The material can be an osteogenic material capable of facilitating bone growth thus enhancing and/or accelerating fusion, such as bone graft material, growth factors, and/or differentiation factors. With enhancement or acceleration of fusion, the patient may have minimal pain and decreased length of post-operative recovery, and thus be able to return to normal activities faster than with use of the implant alone. The bone graft material may be any art-acceptable grafting material, including, but not limited to, autograft, allograft, xenograft, artificial mixtures, synthetic mixtures, demineralized bone matrix, hydroxyapatite mixtures, and combinations thereof.

For some patients, the presence of bone graft material alone may not achieve the rate of growth sufficient for fusion to occur. In these cases, an effective amount of a growth factor, differentiation factor, cytokines, and/or hormones can be added to the bone graft material, including, but not limited to bone morphogenic protein (BMP), transforming growth factor β1 (TGFβ1), insulin-like growth factor 1 (IGF-1), platelet-derived growth factor (PDGF), activin, parathyroid hormone, fibroblast growth factor (FGF), LIM mineralization protein (LMP), and combinations thereof. The inserted material advantageously creates a contiguous contact with the existing bones for optimal fusion to occur. Thus, while material could be inserted into the collapsed implant prior to installation, additional material can be inserted after the implant is installed and prior to closing the incision.

The implant allows infinite expansion and retraction, within practical limits defined by tolerances and precision of manufacturing, over a range specified by about the length of the threaded shafts. Prior to actuation of the gears and threaded shafts, the implant exhibits a compact, retracted, or collapsed configuration. The reduced height has, at least, the advantages of allowing for minimally-invasive insertion rather than an insertion with traditional open surgery, and decreasing impact on tendons, nerves, blood vessels, and other body tissues, when inserted. Thus, the patient receives the benefits of minimally-invasive techniques such as small scars, reduced tissue necrosis, minimized bone dissection, reduced chances of infection, minimized blood loss, reduced trauma to tissues, minimal postoperative pain, shorter hospital stays, shorter recovery periods, and/or reduced costs.

The implant can be incrementally expanded from the reduced position in situ to restore the height and preserve the structure of the disc space. The expansion property of the implant allows for intraoperative positioning and adjusting for each individual patient to achieve a better fit and to decrease postoperative dislodgement. Although the implant does not require any supplemental fixation, postoperative dislodgement may be further avoided with additional fixation of the implant in the body by installation of devices such as rods, screws, and plates. Furthermore, the implant is easily manipulated and is capable of collapse and repositioning as benefits the patient.

The invention also provides methods for using the implant to facilitate arthrodesis or fusion of adjacent spinal vertebrae. Although this method is described and illustrated for fusion of vertebrae, it is suitable for fusion of any adjacent bones or joints, such as the ankle or knee. The method is not limited to the embodiments described herein.

After anesthetizing the patient, a surgical incision is made to access the two adjacent vertebrae to be fused in the patient's body. The surgeon may use a posterior approach, anterior approach, lateral approach, or any other approach deemed appropriate for the patient. The implant is collapsed for insertion. Osteogenic material may be inserted into the hollow spaces at this time, or may be inserted during or after placement of the implant through the apertures in the threaded shafts. For example, in the collapsed configuration, prior to insertion, material may be added into space 57b, and after insertion into spaces 57a, 64a, and/or 64b (FIGS. 5 and 7).

The accessed space between the vertebrae is prepared for insertion of the implant. In preparing the space the surgeon may do one or more of the following: discectomy, dissect and remove bone (laminectomy, laminotomy, and foraminotomy), and reposition or remove cartilage, including removal of all or part of the vertebral endplates and/or cortical bone. The implant is then inserted into the prepared space using any minimally-invasive technique, for example, the collapsed implant can be inserted into a cannula and monitored via endoscope.

Figure 8:
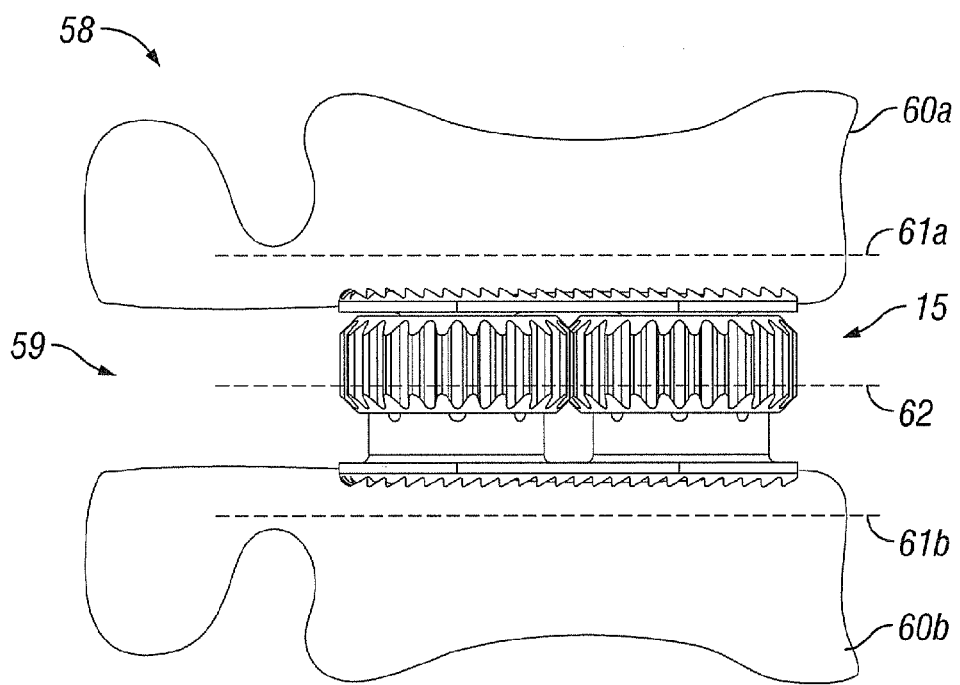
FIG. 8 is a sagittal plane view showing a cross-sectional side view of the implant shown in FIG. 5 inserted between two adjacent vertebrae.

Placement of a collapsed implant 58 into the intervertebral disc space 59 between adjacent vertebrae 60a (top) and 60b (bottom) is illustrated in FIG. 8. The implant 58 may or may not completely fill the intervertebral disc space 59. The alignment of implant 58, represented by lines 61a and 61b, is substantially parallel with longitudinal axis 62. After the implant is correctly positioned in the intervertebral disc space, the pair of gears is mechanically activated via manual or robotic engagement of a tool with the teeth of a gear. The rotation of the gear rotates the shaft to extend the top plate in the direction of the vertebral body. The top plate then contacts the vertebral endplates, cortical bone, and/or the cancellous bone to compress and distract the vertebral bodies.

In order to expose the cancellous bone, removal of all or part of the vertebral endplates and cortical bone layer can be done. It is advantageous for the implant to be in contact with the bone marrow as the bone marrow provides osteoprogenitor cells which enhance the growth and formation of new bone. When proper distraction is achieved the implant is adjusted to a therapeutically-acceptable height for the patient. A "therapeutically-acceptable" height is any height that provides beneficial to the patient, i.e. reduced pain, reduced pressure on nerve roots, restoration of joint function, restoration of motion, and/or repair of diseased or injured conditions. The implant may be collapsed and re-extended if necessary for a better fit if the insertion is not secure or the height is incorrect, or a condition in the patient changes.

Figure 9:
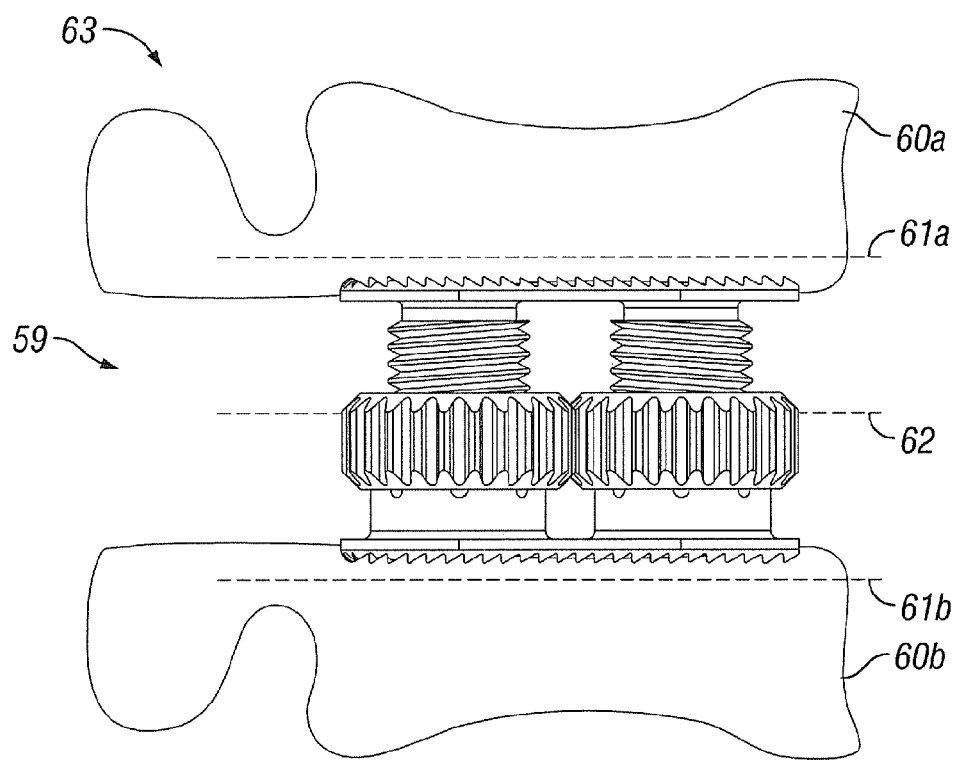
FIG. 9 is a sagittal plane view showing a cross-sectional side view of the implant shown in FIG. 4 in an expanded position.

Furthermore, after surgery, if the implant needs any adjusting or repositioning the gears of the implant may be accessed and adjusted via a minimally-invasive procedure. Thus, the need for replacement implants is decreased, and in turn, decreasing pain and costs for the patient are realized. Positioning of the expanded implant 63 into the intervertebral disc space 59 between adjacent vertebrae 60a (top) and 60b (bottom) is illustrated in FIG. 9. Implant 63 is positioned at an angle such that lines 61a and 61b are no longer parallel with longitudinal axis 62. In this way, the implant 63 restores and maintains the normal curvature (lordosis) of the spine.

After the desired fit is achieved, an adhesive or glue can be applied to prevent further unnecessary rotation of the gears. Although the implant does not require any supplemental fixation with devices such as rods, screws, and plates, these devices can used. When the implant is positioned and secured in the desirable manner, the surgical incision is closed and the patient is allowed to heal.

It should be understood that relative terms such as "top" and "bottom" are provided to aid in understanding the invention; devices in accordance with the invention may be implanted in any orientation the medical practitioner deems best for the patient.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. Drawings are not to scale.

The spacers, implants, methods, procedures, and techniques described herein are presently representative of advantageous embodiments, are intended to be exemplary and are not intended as limitations on the scope. Changes therein and other uses will occur to those skilled in the art which are encompassed within the spirit of the invention and are defined by the scope of appended claims.

Although the invention has been described in connection with specific embodiments, it should be understood that the invention as claimed should not be unduly limited to such specific embodiments. Indeed various modifications of the described modes for carrying out the invention which are obvious to those skilled in the art are intended to be within the scope of the following claims.

What is claimed is:

1. An expandable implant for insertion in a space between adjacent bony structures, comprising:
   a first threaded shaft and a second threaded shaft;
   a base plate coupled to the first threaded shaft and the second threaded shaft; and
   a first gear and a second gear operably coupled with said first threaded shaft and said second threaded shaft, respectively, and operably coupled with said base plate, said first gear and said second gear having respective interior surfaces including threads matably engaged with respective said first threaded shaft and said second threaded shaft, whereby rotation of said first gear and said second gear initiates displacement of said first threaded shaft and said second threaded shaft within said base plate, whereby said first threaded shaft and said second threaded shaft are extendable in a direction away from said base plate;

wherein the first threaded shaft and the second threaded shaft are coupled to a top plate;

wherein the first gear and the second gear are positioned with an axis parallel to the interior surface extending substantially perpendicular to a longitudinal axis of the base plate and adjacent to one another;

wherein the first gear and the second gear are operably coupled to one another whereby rotation of the first gear in a first direction initiates rotation of the second gear in the first direction.

2. The expandable implant according to claim 1, wherein the expandable implant has a first, collapsed height prior to extension of said first threaded shaft and said second threaded shaft and a second, expanded height after extension of said first threaded shaft and said second threaded shaft.

3. The expandable implant according to claim 2, wherein the second, expanded height is adjustable.

4. The expandable implant according to claim 1, wherein the implant is operable to distract the adjacent bony structures.

5. The expandable implant according to claim 1, wherein the space is the intervertebral space between two adjacent spinal vertebrae.

6. The expandable implant according to claim 1, wherein said first threaded shaft and said second threaded shaft each have a hollow interior.

7. The expandable implant according to claim 6, wherein a top end of said first threaded shaft and a top end of said second threaded shaft each include an opening, the opening operable for insertion of material into said hollow interiors.

8. The expandable implant according to claim 7, wherein the material is a bone graft material selected from a group consisting of autograft material, allograft material, xenograft material, artificial mixtures, synthetic mixtures, demineralized bone matrix, hydroxyapatite mixtures, and combinations thereof.

9. The expandable implant according to claim 8, wherein the bone graft material further includes an effective amount of a growth factor or differentiation factor.

10. The expandable implant according to claim 9, wherein the growth factor or differentiation factor is selected from a group consisting of bone morphogenic protein (BMP), transforming growth factor 131 (TGF131), insulin-like growth factor 1 (IGF-1), platelet-derived growth factor (PDGF), activin, parathyroid hormone, fibroblast growth factor (FGF), LIM mineralization protein (LMP), and combinations thereof.

11. The expandable implant according to claim 1, wherein the implant is formed from a material selected from a group consisting of titanium, titanium alloys, stainless steel, chrome cobalt, nickel, ceramics, plastics, shape-memory alloys, bioactive glass, composites, bone, bone substitutes, and combinations thereof.

12. An expandable implant for insertion in a space between adjacent bony structures comprising:
    a first threaded shaft;
    a second threaded shaft;
    a bottom plate having an exterior surface and an interior surface, the interior surface including a base receiving the first threaded shaft and the second threaded shaft; and
    a pair of coupled actuation gears comprising a first gear of the pair having a first interior gear surface operably coupled to the first threaded shaft, further comprising a second gear of the pair having a second interior gear surface operably coupled to the second threaded shaft;
    whereby rotation of the first gear in a first direction initiates rotation of the second gear in a second direction, opposite the first direction, initiating rotation of the first threaded shaft and then the second threaded shaft such that the shafts extend to engage adjacent bony structures;
    wherein the first gear and the second gear are directly coupled to each other and are positioned with a longitudinal axis of the first interior gear surface and a longitudinal axis of the second interior gear surface extending perpendicular to a longitudinal axis of the base plate.

13. The expandable implant according to claim 12, wherein the first threaded shaft and the second threaded shaft are in a substantially parallel configuration.

14. The expandable implant according to claim 12, wherein the base holds the first threaded shaft and the second threaded shaft in an angled configuration.

* * * * *